United States Patent
Kuo et al.

(10) Patent No.: US 10,098,587 B1
(45) Date of Patent: Oct. 16, 2018

(54) PHYSIOLOGY DETECTING GARMENT AND METHOD THEREOF

(71) Applicant: Industrial Technology Research Institute, Hsinchu (TW)

(72) Inventors: Chien-Chih Kuo, Kaohsiung (TW); Tien-Cheng Tseng, Hsinchu County (TW); Pei-Fen Chan, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 15/855,614

(22) Filed: Dec. 27, 2017

(51) Int. Cl.
*A61B 5/00* (2006.01)
*H04W 4/80* (2018.01)
*H01Q 1/27* (2006.01)
*A61B 5/0205* (2006.01)

(52) U.S. Cl.
CPC .......... *A61B 5/6804* (2013.01); *A61B 5/0006* (2013.01); *A61B 5/0015* (2013.01); *H04W 4/80* (2018.02); *A61B 5/0205* (2013.01); *A61B 5/7203* (2013.01); *A61B 2560/0443* (2013.01); *A61B 2562/12* (2013.01); *H01Q 1/273* (2013.01)

(58) Field of Classification Search
CPC ... A61B 5/6804; A61B 5/0006; A61B 5/0015; A61B 5/0205; A61B 5/7203; H04W 4/80
See application file for complete search history.

(56) References Cited

U.S. PATENT DOCUMENTS

| | | | |
|---|---|---|---|
| 6,801,140 B2 | 10/2004 | Mantyjarvi et al. |
| 8,228,202 B2 | 7/2012 | Buchner et al. |
| 8,233,969 B2 | 7/2012 | Muhlsteff et al. |
| 8,591,411 B2 | 11/2013 | Banet et al. |

(Continued)

FOREIGN PATENT DOCUMENTS

| | | | |
|---|---|---|---|
| TW | 200920436 A | 5/2009 |
| TW | 201041531 A1 | 12/2010 |

(Continued)

OTHER PUBLICATIONS

Silva Cunha et al., "Vital Jacket®: A Wearable Wireless Vital Signs Monitor for Patients' Mobility in Cardiology and Sports," 2010 4th Int'l Conference on Pervasive Computing Technologies for Healthcare (PervasiveHealth), Mar. 2010, pp. 1-2, IEEE, US.

(Continued)

*Primary Examiner* — Leon Flores

(57) ABSTRACT

A physiology detecting garment is provided in the invention. The physiology detecting garment includes a garment, a first transmission line, a second transmission line, a first detecting device, a second detecting device, a first textile antenna and a second textile antenna. The first textile antenna is configured in the garment and receives a first sensing signal. The second textile antenna is configured in the garment and receives a second sensing signal. The first detecting device samples the first sensing signal to generate a first time index and the second detecting device samples the second sensing signal to generate a feedback signal. The first detecting device generates a second time index according to the feedback signal, and generates a time parameter according to the first time index and the second time index, and obtains physiological information according to the time parameter.

14 Claims, 5 Drawing Sheets

(56) References Cited

U.S. PATENT DOCUMENTS

| | | | |
|---|---|---|---|
| 9,339,211 B2 | 5/2016 | Banet et al. | |
| 2006/0122544 A1 | 6/2006 | Ciluffo | |
| 2009/0204013 A1* | 8/2009 | Muhlsteff | A41B 9/001 600/506 |
| 2009/0216132 A1 | 8/2009 | Orbach | |
| 2013/0321168 A1* | 12/2013 | Mahony | A61B 5/002 340/870.09 |
| 2014/0343393 A1 | 11/2014 | Lee et al. | |
| 2017/0086510 A1* | 3/2017 | Aleksov | A41D 1/002 |
| 2017/0258402 A1* | 9/2017 | Acquista | A61B 5/6833 |
| 2017/0265743 A1* | 9/2017 | Lin | A61B 5/002 |

FOREIGN PATENT DOCUMENTS

| | | |
|---|---|---|
| TW | I503100 B | 10/2015 |
| TW | M517534 U | 2/2016 |
| TW | 201711578 A | 4/2017 |
| TW | I589269 B | 7/2017 |

OTHER PUBLICATIONS

David M.D. Ribeiro, "A Real Time, Wearable ECG and Continuous Blood Pressure Monitoring System for First Responders," 33 Annual Int'l Conference of the IEEE EMBS, Aug. 2011, pp. 6894-6898, IEEE, US.

Fung et al., "Continuous Noninvasive Blood Pressure Measurment by Pulse Transit Time," Proceedings of the 26th Annual International Conference of the IEEE EMBS, Sep. 2004, pp. 738-741, IEEE, US.

\* cited by examiner

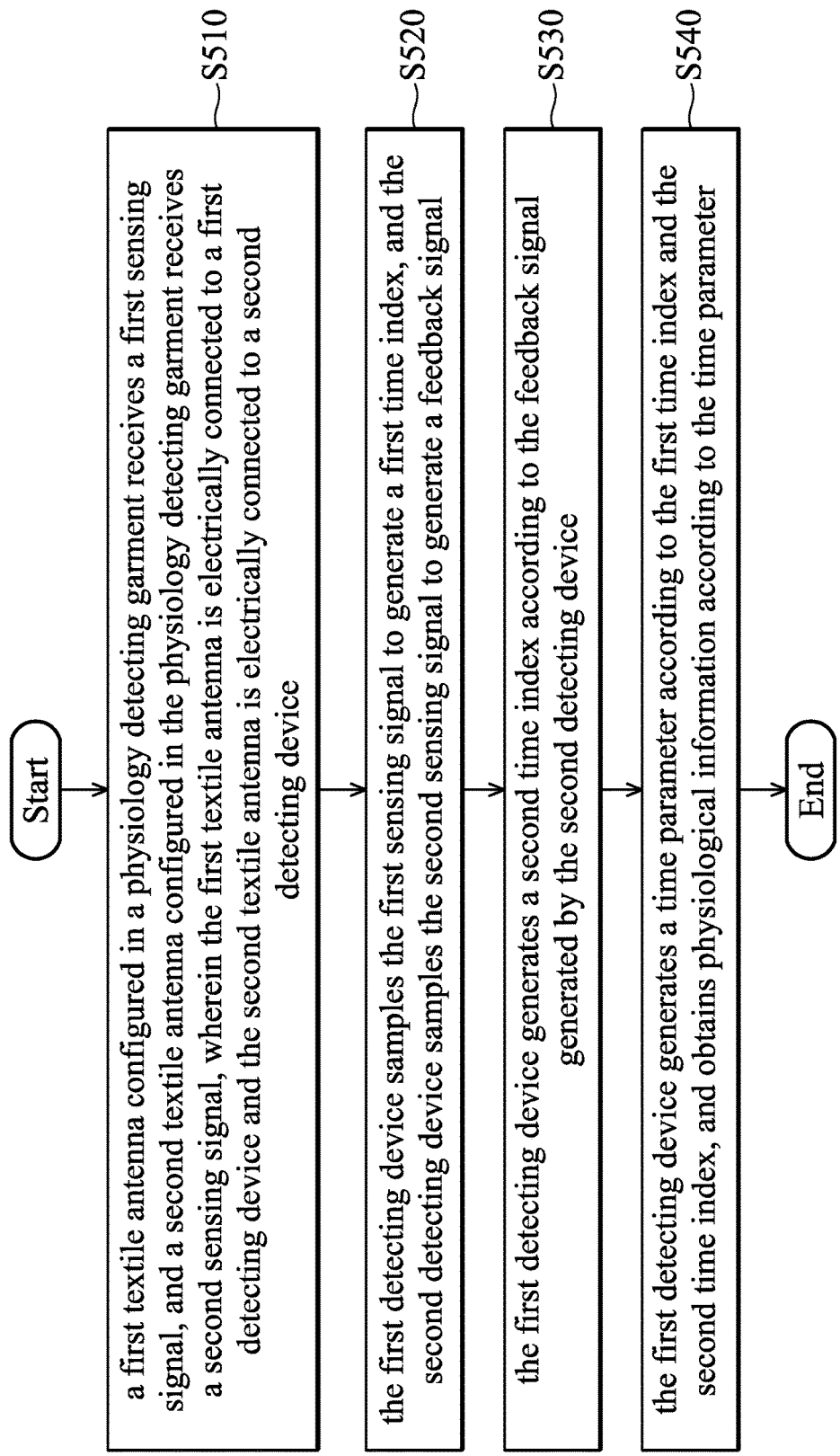

PHYSIOLOGY DETECTING GARMENT AND METHOD THEREOF

TECHNICAL FIELD

The invention generally relates to a physiology detecting technology and method.

BACKGROUND

In conventional Non-Invasive Blood Pressure (NIBP) measurement technologies, a cuff is used to stress the blood vessel to block the blood flow, and then the pressure on the cuff is released gradually and a systolic pressure and a diastolic blood pressure can be measured by detecting the pulse of the blood vessel via stethoscope or another detecting device. However, because the conventional NIBP sphygmomanometer needs to stress the blood vessel with the cuff to measure the blood pressure, as a result, the size of the sphygmomanometer and its accessories may be too big to carry, and the user cannot use the sphygmomanometer to measure the blood pressure continuously for long tune. Furthermore, in conventional NIBP measurement technologies, the cuff is inflated to stress the blood vessel, the sphygmomanometer may generate noise and the user may feel uncomfortable.

Therefore, cuff-less measurement technologies are proposed, wherein in cuff-less measurement technologies, blood pressure is measured according to the pulse transit time (PTT) or pulse wave velocity (PWV) calculated through an Electrocardiogram (ECG) with Photoplethysmography (PPG). However, the EGG needs to use an electrode to touch the skin to measure the weak voltage variety in human skin, and the PPG detects the signals of the blood vessel through the photodetector and is easily affected by the background light source. Therefore, for the usage of the EGG and PGG, the EGG and PGG needs to tightly touch the skin to avoid the background noise which may lead to the degradation of the signal-to-noise-ratio (SNR). Therefore, although the cuff-less measurement technologies may be able to reduce the discomfort generated by the cuff of the conventional NIBP sphygmomanometer, the cuff-less measurement technologies still cannot avoid the need to tightly touch the skin and cannot avoid the errors generated because of the different lengths of blood vessels. In addition, with cuff-less measurement technologies, the user also needs to wear additional accessories which may lead to inconvenience when measuring blood pressure.

BRIEF SUMMARY

A physiology detecting garment and a physiology detecting method are provided to overcome the problems described above.

An embodiment in accordance with the disclosure provides a physiology detecting garment. The physiology detecting garment comprises a garment, a first transmission line, a second transmission line, a first detecting device, a second detecting device, a first textile antenna and a second textile antenna. The first transmission line is configured in the garment. The second transmission line is configured in the garment. The second detecting device is electrically connected to the first detecting device through the first transmission line and the second transmission line. The first textile antenna is configured in the garment, electrically connected to the first detecting device, and receives a first sensing signal. The second textile antenna is configured in the garment, electrically connected to the second detecting device, and receives a second sensing signal. The first detecting device samples the first sensing signal to generate a first time index, and the second detecting device samples the second sensing signal to generate a feedback signal. The first detecting device generates a second time index according to the feedback signal generated by the second detecting device, and the first detecting device generate a time parameter according to the first time index and the second time index, and obtains physiological information according to the time parameter.

An embodiment in accordance with the disclosure provides a physiology detecting method. The physiology detecting method is applied to a physiology detecting garment. The physiology detecting method comprising the steps of receiving a first sensing signal through a first textile antenna configured in the physiology detecting garment and receiving a second sensing signal through a second textile antenna configured in the physiology detecting garment, wherein the first textile antenna is electrically connected to a first detecting device and the second textile antenna is electrically connected to a second detecting device; using the first detecting device to sample the first sensing signal to generate a first time index, and using the second detecting device to sample the second sensing signal to generate a feedback signal by the second detecting device; using the first detecting device to generate a second time index according to the feedback signal generated by the second detecting device; and using the first detecting device to generate a time parameter according to the first time index and the second time index and then using the first detecting device to obtain physiological information according to the time parameter.

Other aspects and features of the invention will become apparent to those with ordinary skill in the art upon review of the following descriptions of specific embodiments of physiology detecting garments and the physiology detecting methods.

BRIEF DESCRIPTION OF THE DRAWINGS

The disclosure will become more fully understood by referring to the following detailed description with reference to the accompanying drawings, wherein:

FIG. 5 is a flowchart illustrating a physiology detecting method according to an embodiment of the disclosure.

DESCRIPTION OF THE EMBODIMENTS

The descriptions of the disclosure are some embodiments for the purpose of illustrating the general principles of the disclosure and should not be configured to limit the disclosure. The scope of the invention is determined by reference to the appended claims.

Figure 1:
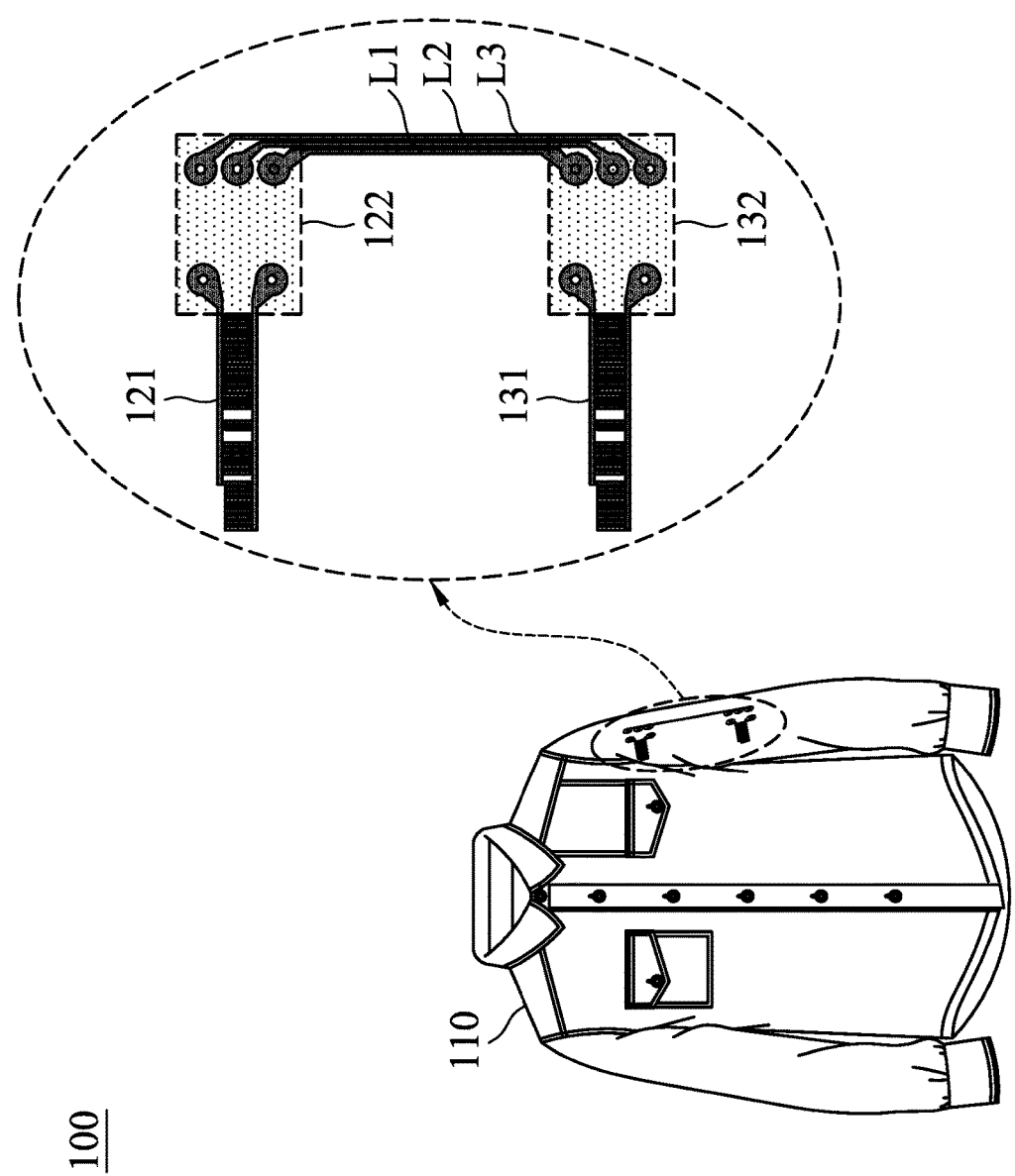
FIG. 1 is a schematic diagram of a physiology detecting garment 100 according to an embodiment of the disclosure.

FIG. 1 is a schematic diagram of a physiology detecting garment 100 according to an embodiment of the disclosure.

As shown in FIG. 1, the physiology detecting garment 100 may include a garment 110, a first textile antenna 121, a first detecting device 122, a first transmission line L1, a second transmission line L2, a third transmission line L3, a second textile antenna 131 and a second detecting device 132. Note that, FIG. 1 presents a simplified schematic diagram in which only the elements relevant to the disclosure are shown. However, the disclosure is not limited to what is shown in FIG. 1. In some embodiments of the disclosure, the physiology detecting garment 100 may include other textile antennas and detecting devices.

According to an embodiment of the disclosure, the first textile antenna 121 and the second textile antenna 131 may be configured in the garment 110, and the first textile antenna 121 and the second textile antenna 131 are made up by an electrically conductive composition. The electrically conductive composition may comprise a nanowire and a polyurethane (PU) polymer, but the disclosure is not limited thereto. In some embodiment of the disclosure, the electrically conductive composition may further comprise a conductive adhesive. Furthermore, according to an embodiment of the disclosure, the first textile antenna 121 and the second textile antenna 131 are bounded to the garment 110 by the thermal-compression method.

Figure 2:
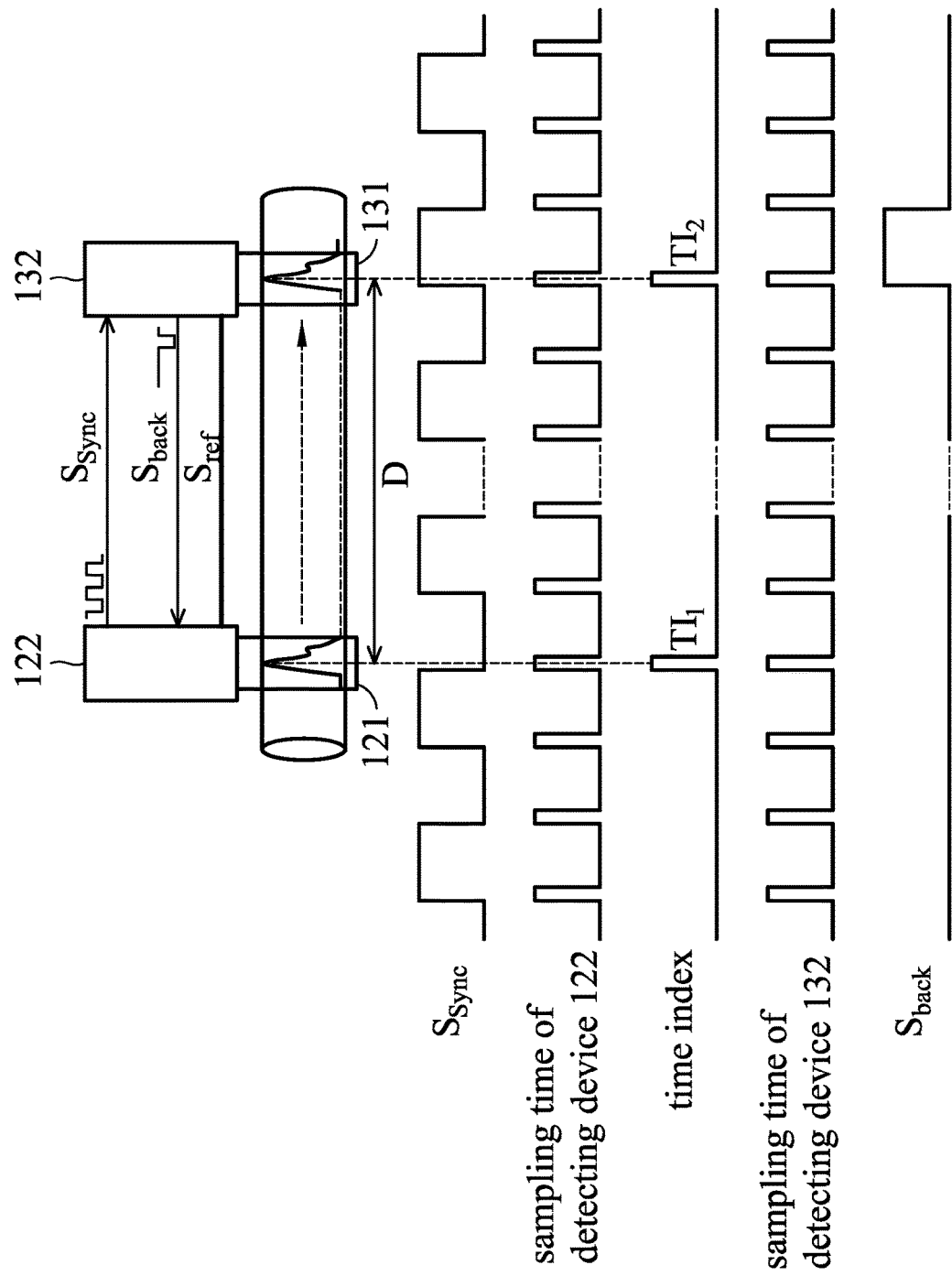
FIG. 2 is a controlling timing diagram of a first detecting device and second detecting device according to an embodiment of the disclosure.

Referring to FIG. 2, according to an embodiment of the disclosure, the first transmission line L1, the second transmission line L2, and the third transmission line L3 may be configured in the garment 110, and the first textile antenna 121 and the second textile antenna 131 are made up by an electrically conductive composition. According to an embodiment of the disclosure, the first transmission line L1, the second transmission line L2, and the third transmission line L3 are textile transmission lines. According to an embodiment of the disclosure, the first transmission line L1 is configured to provide a reference signal $S_{ref}$ to the first detecting device 122 and the second detecting device 132. The first detecting device 122 and the second detecting device 132 may obtain a reference voltage. According to an embodiment of the disclosure, the second transmission line L2 is configured to transmit a feedback signal $S_{back}$ from the second detecting device 132 to the first detecting device 122. The third transmission line L3 is configured to transmit a synchronous signal $S_{sync}$ from the first detecting device 122 to the second detecting device 132.

According to an embodiment of the disclosure, the first detecting device 122 and the second detecting device 132 detect the physiological signal of a wearer of the physiology detecting garment 100 through a Nanosecond Pulse Near-field Sensing (NPNS) technology. The first detecting device 122 may transmit a pulse signal to human body through the first textile antenna 121 and receive the reflected signal (i.e. first sensing signal) from the human body through the first textile antenna 121. The second detecting device 132 may transmit a pulse signal to human body through the second textile antenna 131 and receive the reflected signal (i.e. second sensing signal) from the human body through the second textile antenna 131.

According to an embodiment of the disclosure, when an analysis is performed for the physiological signal of the wearer of the physiology detecting garment 100, the first detecting device 122 may transmit a synchronous signal $S_{sync}$ to the second detecting device 132 through the third transmission line L3 first. Then, the first detecting device 122 may sample and analyze the first sensing signal, which is received from the first textile antenna 121, according to the synchronous signal $S_{sync}$ and the first sensing signal to generate a first time index $TI_1$. When the second detecting device 132 receives the synchronous signal $S_{sync}$, the second detecting device 132 may sample and analyze the second sensing signal, which is received from the second textile antenna 131, according to the synchronous signal $S_{sync}$ and the second sensing signal to generate a feedback signal $S_{back}$. The second detecting device 132 may transmit the feedback signal $S_{back}$ to the first detecting device 122 through the second transmission line L2. After the first detecting device 122 receive the feedback signal $S_{back}$, the first detecting device 122 may generate a second time index $TI_2$ according to the time point corresponding to generate the feedback signal $S_{back}$.

Backing to FIG. 2, the first detecting device 122 may generate a time parameter (i.e. Pulse Transmit Time (PTT)) according to the first time index $TI_1$ and the second time index $TI_2$. Specifically, the first detecting device 122 may obtain the PTT according to the time difference between the first time index $TI_1$ and the second time index $TI_2$. After obtaining the time parameter, the first detecting device 122 may obtain a physiological parameter (i.e. Pulse Wave Velocity (PWV), wherein PWV=D/PTT) according to the time parameter and a distance D between the first textile antenna 121 and the second textile antenna 131. After the first detecting device 122 obtains the physiological parameter, the first detecting device 122 may transform the physiological parameter to the physiological information corresponding to the physiological signal of the wearer of the physiology detecting garment 100, e.g. blood pressure value. In another embodiment of the disclosure, the first detecting device 122 may directly transform the time parameter to the physiological information corresponding to the physiological signal of the wearer of the physiology detecting garment 100, e.g. blood pressure value. For example, the first detecting device 122 may directly transform the time parameter to the physiological information according to a look-up table.

According to another embodiment of the disclosure, the first detecting device 122 may sample and analyze the first sensing signal, which is received from the first textile antenna 121, according to the synchronous signal $S_{sync}$ and the first sensing signal to generate a feedback signal $S_{back}$ and then the first detecting device 122 may transmit the feedback signal $S_{back}$ to the second detecting device 132 through the second transmission line L2. After the second detecting device 132 receive the feedback signal $S_{back}$, the second detecting device 132 may generate a first time index $TI_1$ according to the time point corresponding to generate the feedback signal $S_{back}$. Then, the second detecting device 132 may obtain the physiological parameter according to the first time index $TI_1$, the second time index $TI_2$ and the distance D between the first textile antenna 121 and the second textile antenna 131. After the second detecting device 132 obtains the physiological parameter, the second detecting device 132 may transform the physiological parameter to the physiological information corresponding to the physiological signal of the wearer of the physiology detecting garment 100, e.g. blood pressure value. In another embodiment of the disclosure, the second detecting device 132 may directly transform the time parameter to the physiological information corresponding to the physiological signal of the wearer of the physiology detecting garment 100, e.g. blood pressure value. For example, the second detecting device 132 may directly transform the time parameter to the physiological information according to a look-up table.

FIG. 2 is a controlling timing diagram of a first detecting device and second detecting device according to an embodiment of the disclosure. Referring to FIGS. 1 and 2, when an analysis is performed for the physiological signal of the wearer of the physiology detecting garment 100, the first detecting device 122 may transmit a continuous square wave signal (i.e. synchronous signal $S_{sync}$) to the second detecting device 132 through the third transmission line L3 first. The first detecting device 122 may take the positive-edge and the negative-edge of the continuous square wave signal (i.e. synchronous signal $S_{sync}$) to be the reference timing. That is to say, the first detecting device 122 may sample the first sensing signal, which is received from the first textile antenna 121, at the positions of the positive-edge and the negative-edge of the continuous square wave signal (i.e. synchronous signal $S_{sync}$). Furthermore, the first detecting device 122 may analyze the sampled first sensing signals. When the first detecting device 122 detects that the sampled first sensing signal is a peak of a wave signal, the first detecting device 122 may generate a first time index $TI_1$. Similarly, when the second detecting device 132 receives the synchronous signal $S_{sync}$, the second detecting device 132 may also take the positive-edge and the negative-edge of the continuous square wave signal (i.e. synchronous signal $S_{sync}$) to be the reference timing, and sample the second sensing signal, which is received from the second textile antenna 131, at the positions of the positive-edge and the negative-edge of the continuous square wave signal (i.e. synchronous signal $S_{sync}$). Furthermore, the second detecting device 132 may also analyze the sampled second sensing signals. When the second detecting device 132 detects that the sampled second sensing signal is a peak of a wave signal, the second detecting device 132 may generate a feedback signal $S_{back}$ and transmits the feedback signal $S_{back}$ to the first detecting device 122 through the second transmission line L2. When the first detecting device 122 receives the feedback signal $S_{back}$, the first detecting device 122 may generate a second time index $TI_2$ according to the time point corresponding to generate the feedback signal $S_{back}$. In addition, as shown in FIG. 2, the first transmission line L1 may provide a reference signal $S_{ref}$ to the first detecting device 122 and the second detecting device 132.

Figure 3:
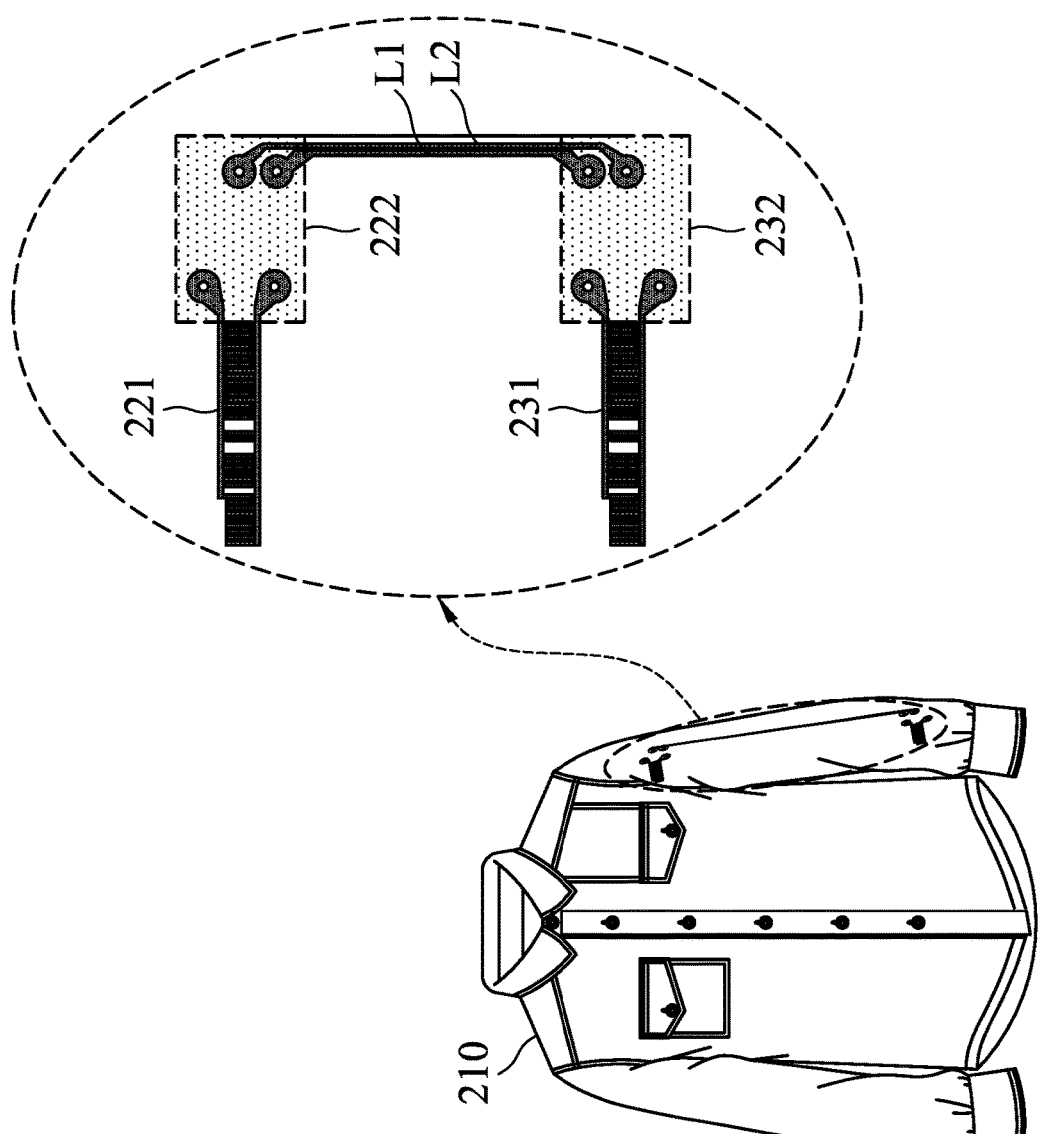
FIG. 3 is a schematic diagram of a physiology detecting garment 200 according to another embodiment of the disclosure.

FIG. 3 is a schematic diagram of a physiology detecting garment 200 according to another embodiment of the disclosure. As shown in FIG. 3, the physiology detecting garment 200 may include a garment 210, a first textile antenna 221, a first detecting device 222, a first transmission line L1, a second transmission line L2, a second textile antenna 231 and a second detecting device 232. Note that, FIG. 3 presents a simplified schematic diagram in which only the elements relevant to the disclosure are shown. However, the disclosure is not limited to what is shown in FIG. 3. In some embodiments of the disclosure, the physiology detecting garment 200 may include other textile antennas and detecting devices.

The first textile antenna 221 and the second textile antenna 231 of the embodiment are similar to the first textile antenna 121 and the second textile antenna 131 shown in FIG. 1, and the first detecting device 222 and the second detecting device 232 are similar to the first detecting device 122 and the second detecting device 132 shown in FIG. 1, therefore, the details will not be illustrated repeatedly herein.

In addition, unlike the physiology detecting garment 100 of FIG. 1, in the embodiment, the physiology detecting garment 200 only comprises a first transmission line L1 and a second transmission line L2.

Figure 4:
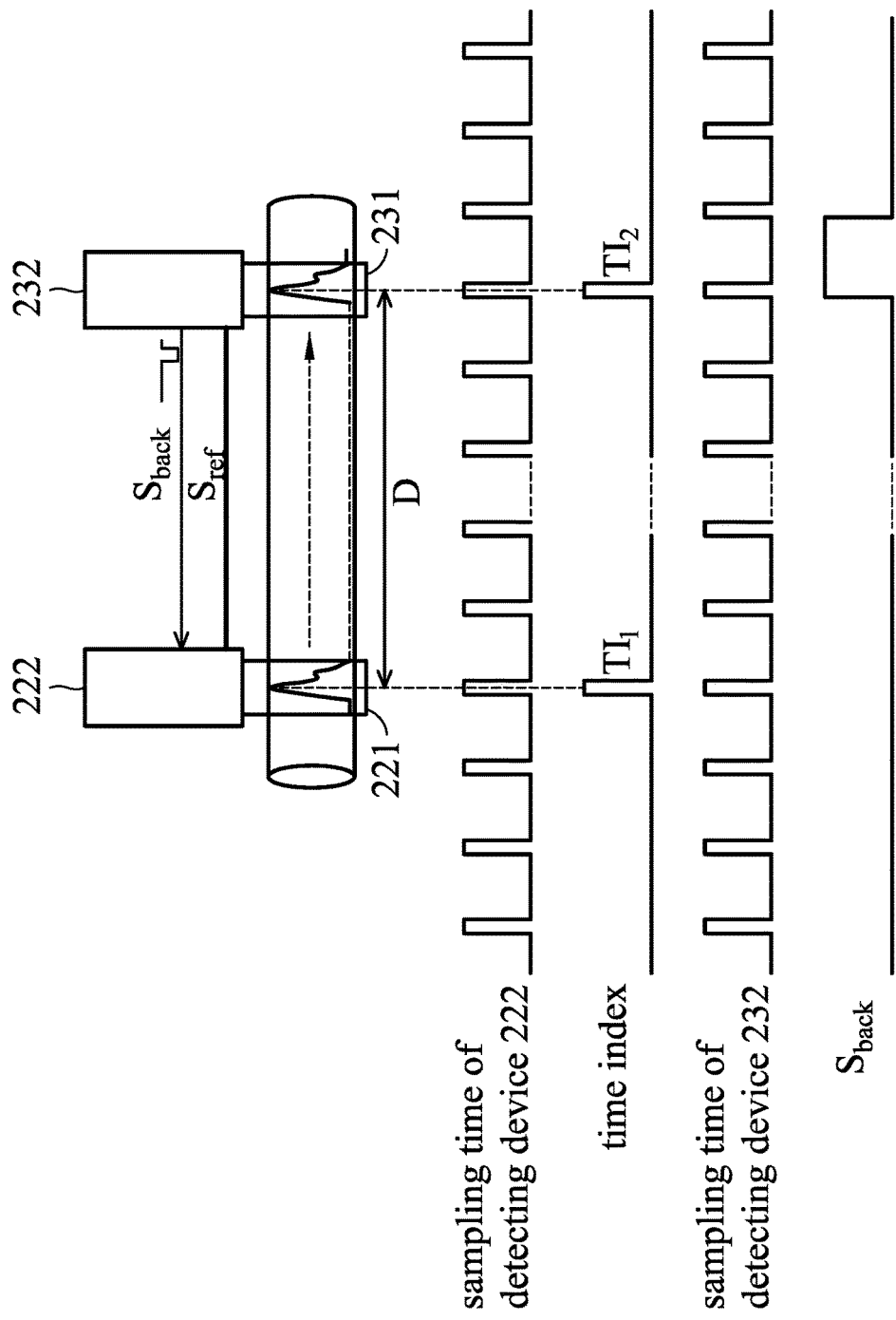
FIG. 4 is a controlling timing diagram of a first detecting device and second detecting device according to another embodiment of the disclosure.

According to an embodiment of the disclosure, when an analysis is performed for the physiological signal of the wearer of the physiology detecting garment 200, the first detecting device 222 may sample and analyze the first sensing signal, which is received from the first textile antenna 221, according to a fixed sampling frequency to generate a first time index $TI_1$. The second detecting device 232 may also sample and analyze the second sensing signal, which is received from the second textile antenna 231, according to the fixed sampling frequency to generate a feedback signal $S_{back}$. The second detecting device 232 may transmit the feedback signal $S_{back}$ to the first detecting device 222 through the second transmission line L2. After the first detecting device 222 receive the feedback signal $S_{back}$, the first detecting device 222 may generate a second time index $TI_2$ according to the corresponding time point to generate the feedback signal $S_{back}$. FIG. 4 is taken for illustration below.

The first detecting device 222 may generate a time parameter (i.e. Pulse Transmit Time (PTT)) according to the first time index $TI_1$ and the second time index $TI_2$. Specifically, the first detecting device 222 may obtain the PTT according to the time difference between the first time index $TI_1$ and the second time index $TI_2$. After obtaining the time parameter, the first detecting device 222 may obtain a physiological parameter (i.e. Pulse Wave Velocity (PWV), wherein PWV=D/PTT) according to the time parameter and a distance D between the first textile antenna 221 and the second textile antenna 231. After the first detecting device 222 obtains the physiological parameter, the first detecting device 222 may transform the physiological parameter to the physiological information corresponding to the physiological signal of the wearer of the physiology detecting garment 200, e.g. blood pressure value. In another embodiment of the disclosure, the first detecting device 222 may directly transform the time parameter to the physiological information corresponding to the physiological signal of the wearer of the physiology detecting garment 200, e.g. blood pressure value. For example, the first detecting device 222 may directly transform the time parameter to the physiological information according to a look-up table.

According to another embodiment of the disclosure, the first detecting device 222 may sample and analyze the first sensing signal, which is received from the first textile antenna 221, according to the fixed sampling frequency to generate a feedback signal $S_{back}$ and then the first detecting device 222 may transmit the feedback signal $S_{back}$ to the second detecting device 232 through the second transmission line L2. After the second detecting device 232 receive the feedback signal $S_{back}$, the second detecting device 232 may generate a first time index $TI_1$ according to the time point corresponding to generate the feedback signal $S_{back}$. Then, the second detecting device 232 may obtain the physiological parameter according to the first time index $TI_1$, the second time index $TI_2$ and the distance D between the first textile antenna 221 and the second textile antenna 231. After the second detecting device 232 obtains the physiological parameter, the second detecting device 232 may transform the physiological parameter to the physiological information corresponding to the physiological signal of the wearer of the physiology detecting garment 200, e.g. blood pressure value. In another embodiment of the disclosure, the second detecting device 232 may directly transform the time parameter to the physiological information corresponding to the physiological signal of the wearer of the physiology detecting garment 200, e.g. blood pressure value. For example, the second detecting device 232 may directly transform the time parameter to the physiological information according to a look-up table.

FIG. 4 is a controlling timing diagram of a first detecting device and second detecting device according to another embodiment of the disclosure. Referring to FIGS. 3 and 4, when an analysis is performed for the physiological signal of the wearer of the physiology detecting garment 200, the first detecting device 222 may sample the first sensing signal, which is received from the first textile antenna 221, according to a fixed sampling frequency. Furthermore, the first detecting device 222 may analyze the sampled first sensing signals. When the first detecting device 222 detects that the sampled first sensing signal is a peak of a wave signal, the first detecting device 222 may generate a first time index $TI_1$. Similarly, the second detecting device 232 may also sample the second sensing signal, which is received from the second textile antenna 231, according to the same fixed sampling frequency as first detecting device 222. Furthermore, the second detecting device 232 may also analyze the sampled second sensing signals. When the second detecting device 232 detects that the sampled second sensing signal is a peak of a wave signal, the second detecting device 232 may generate a feedback signal $S_{back}$ and transmits the feedback signal $S_{back}$ to the first detecting device 222 through the second transmission line L2. When the first detecting device 222 receives the feedback signal $S_{back}$, the first detecting device 222 may generate a second time index $TI_2$ according to the time point corresponding to generate the feedback signal $S_{back}$. In addition, as shown in FIG. 4, the first transmission line L1 may provide a reference signal $S_{ref}$ to the first detecting device 222 and the second detecting device 232.

In addition, as shown in FIGS. 1 and 3, the first textile antenna 121 and second textile antenna 131 are configured on the positions corresponding to the left upper arm and the middle of the left arm of the wearer of the physiology detecting garment 100, and the first textile antenna 221 and second textile antenna 231 are configured on the positions corresponding to the positions corresponding to the left upper arm and near the left wrist of the wearer of the physiology detecting garment 200, but the disclosure is not limited thereto. In some embodiments of the disclosure, the first textile antennas 121 and 221 and the second textile antennas 131 and 231 also can be configured in different positions of the physiology detecting garment, e.g. right arm, neck, wrist, and so on. Furthermore, in some embodiments of the disclosure, a single detecting device may be utilized to measure the heartbeat, breath and other physiological information of the wearer of the physiology detecting garment.

FIG. 5 is a flowchart illustrating a physiology detecting method according to an embodiment of the disclosure. The physiology detecting method can be applied to a physiology detecting garment (e.g. the physiology detecting garments 100 and 200). As shown in FIG. 5, in step S510, a first textile antenna configured in a physiology detecting garment receives a first sensing signal, and a second textile antenna configured in the physiology detecting garment receives a second sensing signal, wherein the first textile antenna is electrically connected to a first detecting device and the second textile antenna is electrically connected to a second detecting device. In step S520, the first detecting device samples the first sensing signal to generate a first time index, and the second detecting device samples the second sensing signal to generate a feedback signal. In step S530, the first detecting device generates a second time index according to the feedback signal generated by the second detecting device. In step S540, the first detecting device generates a time parameter according to the first time index and the second time index, and obtains physiological information according to the time parameter.

In some embodiments of the disclosure, the physiology detecting method further comprises that the first detecting device obtains a physiological parameter according to the time parameter and the distance between the first textile antenna and the second textile antenna, and then obtains physiological information according to the physiological parameter.

In some embodiments of the disclosure, the physiology detecting method further comprises that the first detecting device samples the first sensing signal according to a fixed sampling frequency and analyzes the sampled first sensing signal to generate the first time index, and the second detecting device samples the second sensing signal according to the fixed sampling frequency and analyzes the sampled second sensing signal to generate the feedback signal.

In some embodiments of the disclosure, the physiology detecting method further comprises that a synchronous signal is transmitted through a transmission line (i.e. the third transmission line) configured in the physiology detecting garment. In the embodiments, the physiology detecting method further comprises that the first detecting device samples the first sensing signal according to the synchronous signal to generate the first time index, and the second detecting device samples the second sensing signal according to the synchronous signal to generate the feedback signal.

In conventional cuff-less measurement technologies in which the blood pressure is measured according to the pulse transit time (PTT) or pulse wave velocity (PWV) calculated through the Electrocardiogram (ECG) with the Photoplethysmography (PPG), although the cuff-less measurement technologies may be able to reduce the discomfort generated by the cuff of the conventional NIBP sphygmomanometer, the cuff-less measurement technologies still cannot avoid the need to tightly touch the skin and cannot avoid errors being generated because of the different lengths of the blood vessels. According to the physiology detecting garments and the physiology detecting methods provided in the disclosure, in the physiology detecting garments based on the NPNS technology, the textile antennas and the transmission lines may be utilized to connect to the detecting devices to measure the user's physiological parameter (i.e. PWV) though a cuff-less and non-touch measurement method. Then, the user's physiological parameter may be transformed to the physiological information (e.g. blood pressure value). Therefore, the physiology detecting garments and the physiology detecting methods provided in the disclosure may reduce the discomfort of the user and increase the convenience when measuring user's physiological information.

Use of ordinal terms such as "first", "second", "third", etc., in the disclosure and claims is for description. It does not by itself connote any order or relationship.

The above paragraphs describe many aspects. Accordingly, the teaching of the disclosure may be accomplished by many methods, and any configurations or functions in the disclosed embodiments only present a representative condition. Those who are skilled in this technology will understand that all of the disclosed aspects in the disclosure may be applied independently or be incorporated.

While the disclosure has been described by way of example and in terms of preferred embodiment, it is to be understood that the disclosure is not limited thereto. Those who are skilled in this technology can still make various alterations and modifications without departing from the scope and spirit of this disclosure. Therefore, the scope of the present disclosure shall be defined and protected by the following claims and their equivalents.

What is claimed is:

1. A physiology detecting garment, comprising:
   a garment;
   a first transmission line, configured in the garment;
   a second transmission line, configured in the garment;
   a first detecting device;
   a second detecting device, electrically connected to the first detecting device through the first transmission line and the second transmission line;
   a first textile antenna, configured in the garment, electrically connected to the first detecting device, and receiving a first sensing signal; and
   a second textile antenna, configured in the garment, electrically connected to the second detecting device, and receiving a second sensing signal,
   wherein the first detecting device samples the first sensing signal to generate a first time index, and the second detecting device samples the second sensing signal to generate a feedback signal, and
   wherein the first detecting device generates a second time index according to the feedback signal generated by the second detecting device, and the first detecting device generates a time parameter according to the first time index and the second time index, and obtains physiological information according to the time parameter.

2. The physiology detecting garment of claim 1, wherein the first transmission line provides a reference signal to the first detecting device and the second detecting device.

3. The physiology detecting garment of claim 1, wherein the second detecting device transmits the feedback signal to the first detecting device through the second transmission line.

4. The physiology detecting garment of claim 1, wherein the first detecting device obtains a physiological parameter according to the time parameter and a distance between the first textile antenna and the second textile antenna, and the first detecting device obtains the physiological information according to the physiological parameter.

5. The physiology detecting garment of claim 1, wherein the first detecting device samples the first sensing signal according to a fixed sampling frequency to generate the first time index, and the second detecting device samples the second sensing signal according to the fixed sampling frequency to generate the feedback signal.

6. The physiology detecting garment of claim 1, further comprising:
   a third transmission line, configured in the garment and electrically connected to the first detecting device and the second detecting device, wherein the first detecting device transmit a synchronous signal to the second detecting device.

7. The physiology detecting garment of claim 6, wherein the first detecting device samples the first sensing signal according to the synchronous signal to generate the first time index, and the second detecting device samples the second sensing signal according to the synchronous signal to generate the feedback signal.

8. A physiology detecting method, applied to a physiology detecting garment, comprising:
   receiving a first sensing signal through a first textile antenna configured in the physiology detecting garment and receiving a second sensing signal through a second textile antenna configured in the physiology detecting garment, wherein the first textile antenna is electrically connected to a first detecting device and the second textile antenna is electrically connected to a second detecting device;
   sampling, by the first detecting device, the first sensing signal to generate a first time index, and sampling, by the second detecting device, the second sensing signal to generate a feedback signal;
   generating, by the first detecting device, a second time index according to the feedback signal generated by the second detecting device; and
   generating, by the first detecting device, a time parameter according to the first time index and the second time index, and obtaining, by the first detecting device, physiological information according to the time parameter.

9. The physiology detecting method of claim 8, further comprising:
   providing a reference signal to the first detecting device and the second detecting device through a first transmission line.

10. The physiology detecting method of claim 8, further comprising:
    transmitting the feedback signal through the second transmission line.

11. The physiology detecting method of claim 8, further comprising:
    obtaining a physiological parameter according to the time parameter and a distance between the first textile antenna and the second textile antenna; and
    obtaining the physiological information according to the physiological parameter.

12. The physiology detecting method of claim 8, further comprising:
    sampling the first sensing signal according to a fixed sampling frequency to generate the first time index; and
    sampling the second sensing signal according to the fixed sampling frequency to generate the feedback signal.

13. The physiology detecting method of claim 8, further comprising:
    transmitting a synchronous signal through a third transmission line.

14. The physiology detecting method of claim 13, further comprising:
    sampling the first sensing signal according to the synchronous signal to generate the first time index; and
    sampling the second sensing signal according to the synchronous signal to generate the feedback signal.

* * * * *